(12) United States Patent
Boutelle

(10) Patent No.: US 11,268,943 B2
(45) Date of Patent: Mar. 8, 2022

(54) DISSOLVED OXYGEN MEASUREMENT

(71) Applicant: Hach Company, Loveland, CO (US)

(72) Inventor: Steven James Boutelle, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 440 days.

(21) Appl. No.: 16/128,326

(22) Filed: Sep. 11, 2018

(65) Prior Publication Data

US 2020/0080982 A1 Mar. 12, 2020

(51) Int. Cl.
| | |
|---|---|
| G01N 31/22 | (2006.01) |
| G01N 21/63 | (2006.01) |
| G01N 33/18 | (2006.01) |
| G01N 21/64 | (2006.01) |
| G01N 35/00 | (2006.01) |

(52) U.S. Cl.
CPC ......... *G01N 33/1806* (2013.01); *G01N 21/64* (2013.01); *G01N 35/00693* (2013.01); *G01N 35/00722* (2013.01); *G01N 2035/00891* (2013.01)

(58) Field of Classification Search
None
See application file for complete search history.

(56) References Cited

U.S. PATENT DOCUMENTS 5,580,527 A * 12/1996 Bell .................... C08F 8/42
252/301.26

9,709,499 B1 7/2017 Crafton et al.
2002/0164813 A1 11/2002 Colvin et al.
2004/0114137 A1 * 6/2004 Mader .................... G01N 21/77
356/318

FOREIGN PATENT DOCUMENTS

WO 0240972 A1 5/2002

OTHER PUBLICATIONS

International Searching Authority, Notification of Transmittal of the International Search Report and the Written Opinion of the International Searching Authority, or the Declaration, dated Oct. 31, 2019, pp. 12.

* cited by examiner

*Primary Examiner* — Paul S Hyun
(74) *Attorney, Agent, or Firm* — Ference & Associates LLC

(57) ABSTRACT

An embodiment provides a method for measuring dissolved oxygen of an aqueous sample, including: introducing an aqueous sample into a measurement device comprising at least two dissolved oxygen sensors, wherein at least one of the at least two dissolved sensors comprises a trend sensor and at least another of the at least two dissolved sensors comprises a reference sensor; measuring a first value of dissolved oxygen using the trend sensor, wherein the trend sensor samples at a trend frequency; measuring a second value of dissolved oxygen from a reference sensor, wherein the reference sensor samples at a reference frequency, the reference frequency being less than the trend frequency; and correcting the first value of dissolved oxygen based upon the second value of dissolved oxygen. Other aspects are described and claimed.

16 Claims, 3 Drawing Sheets

| Item | Description |
|---|---|
| 1 | Blue LED |
| 2 | Blue Filter, Narrow Bandpass |
| 3 | Red LED |
| 4 | Detector |
| 5 | Red Filter, Narrow Bandpass |
| 6 | Trend Optical Channel |
| 7 | Trend Sensor |
| 8 | Reference Optical Channel |
| 9 | Reference Sensor |
| 10 | Probe Electronics |

DISSOLVED OXYGEN MEASUREMENT

FIELD

This application relates generally to water quality testing, and, more particularly, to measurement of dissolved oxygen.

BACKGROUND

Measurement of dissolved oxygen is important to ensure water quality. Applications for dissolved oxygen measurement may include waste water treatment, drinking water treatment, monitoring natural bodies of water, aqua farming, beverage/food manufacturing, boiler systems, industrial processes, petrochemical processes, chemical tanks, or the like. Dissolved oxygen may be important for aquatic life and viability of natural bodies of water. Additionally, proper levels of dissolved oxygen may be necessary in manufacturing or processing operations such that reactions or processes within the operations properly occur. Proper measurement of dissolved oxygen may also be important for gaseous levels such as high purity gas environments, flue gases, medical gas applications, hazardous gases, or the like.

Measurement of dissolved oxygen may be achieved through specialized probes that may have a service life. Specifically, the probes may degrade over time, which may lead to inaccurate dissolved oxygen measurement. Thus, facilities may spend resources to replace or maintain probes. Since, probes may be located in a hazardous or inaccessible location it may be difficult for the facility to maintain or replace the probe. Despite advances in dissolved oxygen probe design, the maintenance and calibration of the probes remain difficult for facilities.

BRIEF SUMMARY

In summary, one embodiment provides a method for measuring dissolved oxygen of an aqueous sample, comprising: introducing an aqueous sample into a measurement device comprising at least two dissolved oxygen sensors, wherein at least one of the at least two dissolved sensors comprises a trend sensor and at least another of the at least two dissolved sensors comprises a reference sensor; measuring a first value of dissolved oxygen using the trend sensor, wherein the trend sensor samples at a trend frequency; measuring a second value of dissolved oxygen from a reference sensor, wherein the reference sensor samples at a reference frequency, the reference frequency being less than the trend frequency; and correcting the first value of dissolved oxygen based upon the second value of dissolved oxygen.

Another embodiment provides a measurement device for measuring dissolved oxygen of an aqueous sample, comprising: at least one chamber; at least two dissolved oxygen sensors; a processor; and a memory device that stores instructions executable by the processor to: introduce an aqueous sample into a measurement device comprising at least two dissolved oxygen sensors, wherein at least one of the at least two dissolved sensors comprises a trend sensor and at least another of the at least two dissolved sensors comprises a reference sensor; measure a first value of dissolved oxygen using the trend sensor, wherein the trend sensor samples at a trend frequency; measure a second value of dissolved oxygen from a reference sensor, wherein the reference sensor samples at a reference frequency, the reference frequency being less than the trend frequency; and correct the first value of dissolved oxygen based upon the second value of dissolved oxygen.

A further embodiment provides a product for measuring dissolved oxygen of an aqueous sample, comprising: a storage device having code stored therewith, the code being executable by the processor and comprising: code that introduces an aqueous sample into a measurement device comprising at least two dissolved oxygen sensors, wherein at least one of the at least two dissolved sensors comprises a trend sensor and at least another of the at least two dissolved sensors comprises a reference sensor; code that measures a first value of dissolved oxygen using the trend sensor, wherein the trend sensor samples at a trend frequency; code that measures a second value of dissolved oxygen from a reference sensor, wherein the reference sensor samples at a reference frequency, the reference frequency being less than the trend frequency; and code that corrects the first value of dissolved oxygen based upon the second value of dissolved oxygen.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
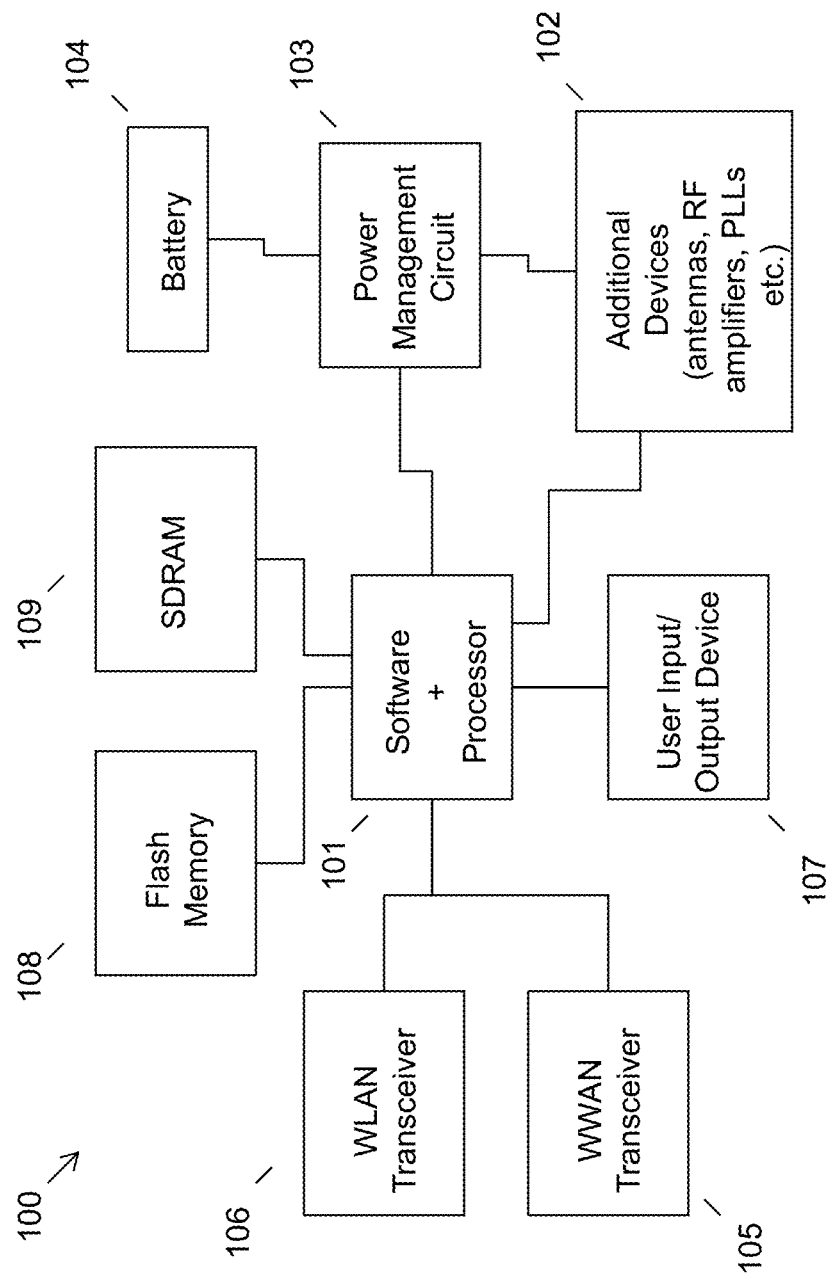
FIG. 1 illustrates an example of computer circuitry

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

The measurement of dissolved oxygen may be critical for the proper treatment or processing of aqueous liquids. Applications which may require dissolved oxygen measurement may include waste water treatment, drinking water treatment, monitoring natural bodies of water, aqua farming, beverage/food manufacturing, boiler systems, industrial processes, petrochemical processes, chemical tanks, or the like. Accurate determination of dissolved oxygen levels may be useful for ensuring the quality wildlife, or for the proper processing of water in a facility. Measurement of dissolved oxygen in a gaseous environment may also be important. The methods described herein may be used to measure dissolved oxygen in different phases.

Measurement of dissolved oxygen may be accomplished using a probe. The probe may be a luminescent dissolved oxygen probe (LDO). Throughout the disclosure the LDO probe may be referred to as a probe or sensor for measuring dissolved oxygen. LDO probes may be equipped with a measuring light emitting diode (LED) that emits a pulse of light and a photo diode that acts as a light detector. The measuring LED may emit a pulse of blue light irradiating the back of an oxygen sensitive area. The oxygen sensitive area may be coated with a coating material that reacts with luminescence and emits a pulse of red light. The coating may be capable of measuring both an intensity and a timing of a pulse of light. If oxygen is present in a sample, which may be in contact with the coating, then the intensity and timing of the luminescent light emission may be changed. In other words, the more oxygen molecules that come into contact with the coating may change the intensity and time delay of the luminescent light emission. As more oxygen molecules are detected, the intensity may be lowered and the shorter the duration of the red radiation. Changes to intensity and duration may be plotted in a profile curve to determine the value of dissolved oxygen in the sample. The methods of luminescent measurement may be further described in U.S. Pat. No. 6,912,050, which is incorporated by reference in its entirety herein.

However, LDO probes may have some limitations as the constant or periodic exposure to light may degrade the coating. For example, the repeated measurements may cause photo-bleaching of the coating or fluorescent material, for example, porphyrin, in the sensors. As the porphyrin is exposed to light such as blue light, ultraviolet (UV) light, or the like, the sensor may report oxygen level measurements that are higher than what is actually present in the sample. In other words, as the coating degrades, the probe or sensor span changes with respect to the probe calibration that may be stored by the measuring system. This change in sensor performance may produce errors across a measurement range. This change in calibration may require constant monitoring by facility staff and recalibration. Recalibration represents a loss of time and resources for a facility. Additionally, some probes are located in hazardous locations or locations that are difficult to access. Thus, to recalibrate or replace these probes is very difficult and may be very dangerous to workers.

Accordingly, the systems and methods described herein provide a technique for measuring dissolved oxygen in an aqueous environment. Specifically, the systems and methods as described herein may use at least two probes to measure dissolved oxygen such that at least one probe is used to measure dissolved oxygen at a time period of traditional measurement and another of the probes acts as a reference probe that only measures dissolved oxygen periodically. The probes may be luminescent dissolved oxygen (LDO) probes. In an embodiment, an aqueous sample may be introduced into a measurement device that may have a plurality of LDO probes. For example, the measurement device may include a trend LDO probe which samples dissolved oxygen at a trend frequency. Additionally, the measurement device may include a reference LDO probe which samples dissolved oxygen at a reference frequency.

The reference LDO probe may serve as to calibrate the trend LDO probe. In other words, the trend probe may be recalibrated in response to the measurement reading from a reference probe. The reference probe may be shielded from or placed in a location such that light does not fall upon the luminescent material area of the reference LDO probe. LDO probes may undergo degradation and become uncalibrated with expose of light to the luminescent surface area. Thus, the shielding of the reference probe from light may conserve the luminescent properties of the reference probe allowing it to be periodically used to perform a dissolved oxygen measurement and this measurement can be used to recalibrate of a trend probe. Such a measurement device reduces the amount of downtime that is required for recalibration or replacement of the LDO probes, reduces the amount of recalibration that is required, thereby reducing the amount of erroneous measurements, and reduces the need for a person to recalibrate or replace probes which may be located in hazardous or difficult to access locations.

The illustrated example embodiments will be best understood by reference to the figures. The following description is intended only by way of example, and simply illustrates certain example embodiments.

While various other circuits, circuitry or components may be utilized in information handling devices, with regard to an instrument for dissolved oxygen measurement according to any one of the various embodiments described herein, an example is illustrated in FIG. 1. Device circuitry 100 may include a measurement system on a chip design found, for example, a particular computing platform (e.g., mobile computing, desktop computing, etc.) Software and processor(s) are combined in a single chip 101. Processors comprise internal arithmetic units, registers, cache memory, busses, I/O ports, etc., as is well known in the art. Internal busses and the like depend on different vendors, but essentially all the peripheral devices (102) may attach to a single chip 101. The circuitry 100 combines the processor, memory control, and I/O controller hub all into a single chip 101. Also, systems 100 of this type do not typically use SATA or PCI or LPC. Common interfaces, for example, include SDIO and I2C.

There are power management chip(s) 103, e.g., a battery management unit, BMU, which manage power as supplied, for example, via a rechargeable battery 104, which may be recharged by a connection to a power source (not shown). In at least one design, a single chip, such as 101, is used to supply BIOS like functionality and DRAM memory.

System 100 typically includes one or more of a WWAN transceiver 105 and a WLAN transceiver 106 for connecting to various networks, such as telecommunications networks and wireless Internet devices, e.g., access points. Additionally, devices 102 are commonly included, e.g., a transmit and receive antenna, oscillators, RF amplifers, PLLs, etc. System 100 includes input/output devices 107 for data input and display/rendering (e.g., a computing location located away from the single beam system that is easily accessible by a user). System 100 also typically includes various memory devices, for example flash memory 108 and SDRAM 109.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform dissolved oxygen measurement of an aqueous sample.

Figure 2:
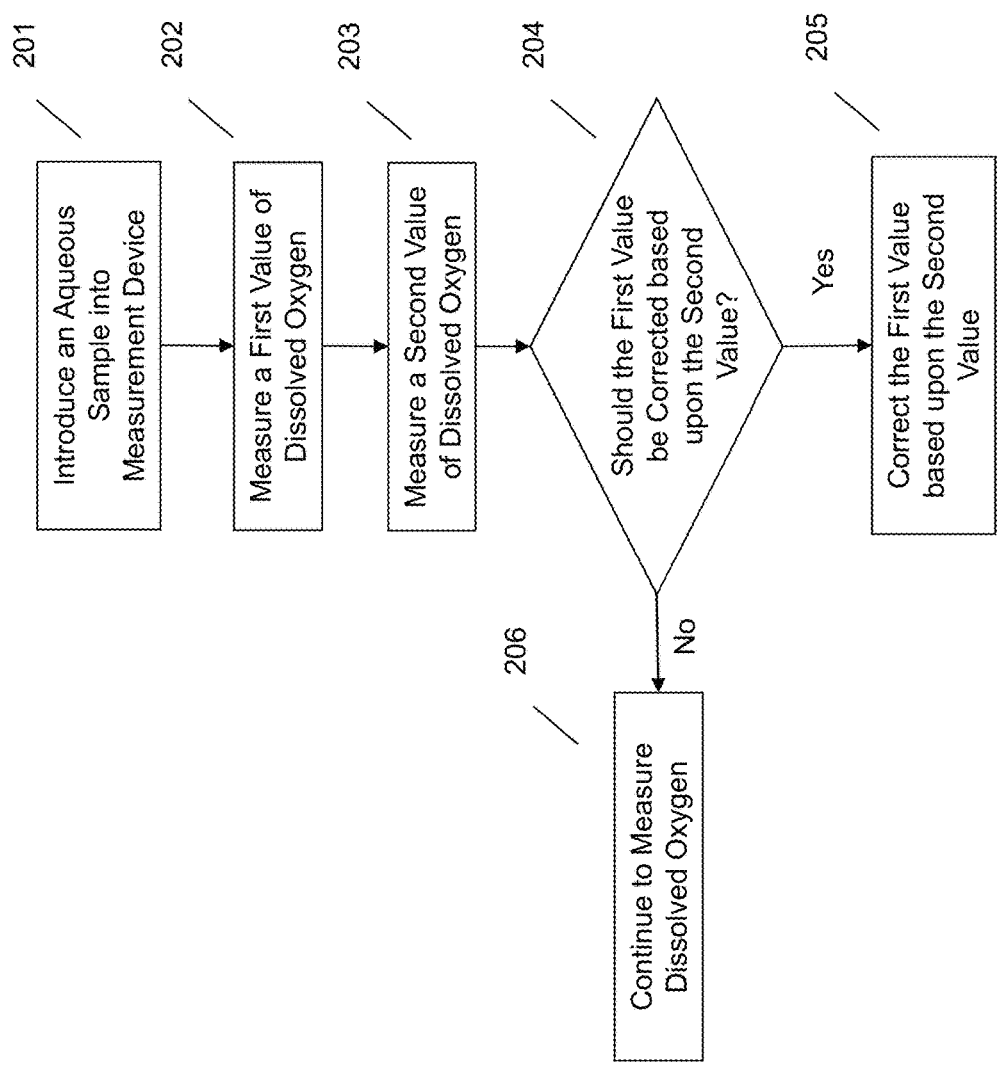
FIG. 2 illustrates a flow diagram of an example dissolved oxygen measuring system.

Referring now to FIG. 2, an embodiment may recalibrate a trend LDO probe using a reference LDO probe included in a measurement device. In an embodiment, a system and method may use a plurality of LDO probes to measure dissolved oxygen in a sample. One probe may be identified as a trend probe that may measure dissolved oxygen levels continuously or at regular intervals as the dissolved oxygen measurements are required. Another probe may be identified as a reference probe that may measure dissolved oxygen in a sample at a frequency lower than the first probe. In an embodiment, the reference probe may be shielded from light, positioned out of light, have a light source turned off, or the like. A reduction in an amount of light that the reference probe is exposed to may lessen the photo-bleaching and subsequent de-calibration of the reference probe. Thus, the reference probe may more accurately measure the dissolved oxygen levels than the trend probe. Accordingly, the reference probe measurement value can be used by the system to recalibrate the trend probe without requiring manual intervention, complex calibration curves, or frequent replacement of probes.

At 201, in an embodiment, a measurement device may be exposed to an aqueous sample. The aqueous sample may include a natural body of water, a holding tank, a processing tank, a pipe, or the like. The aqueous sample may be in a continuous flow, a standing volume of liquid, or any combination thereof. In one embodiment, the aqueous sample may be introduced to a measurement device, for example, a test chamber of the measurement device. Introduction of the aqueous sample into the measurement device may include placing or introducing the aqueous sample into a test chamber manually by a user or using a mechanical means, for example, gravity flow, a pump, pressure, fluid flow, or the like. For example, a water sample for dissolved oxygen testing may be introduced to a measurement or test chamber using a pump. In an embodiment, valves or the like may control the influx and efflux of the aqueous solution into or out of the one or more chambers, if present. Additionally or alternatively, the measurement device may be present or introduced in a volume of the aqueous sample. The measurement device is then exposed to the volume of aqueous sample where it can perform measurements. Once the sample is in contact with the measurement system, the system may measure the dissolved oxygen of the sample, using steps as explained in more detail below. In an embodiment, the measurement device may include one or more chambers in which the one or more method steps may be performed.

The measurement device may include at least two probes for measuring the dissolved oxygen of an aqueous sample. Accordingly, an embodiment may include at least a first probe and a second probe, associated light sources, circuitry to control the system, or the like. The first probe may be identified as a trend probe that may measure dissolved oxygen in a continuous or periodic manner. In other words, the first probe may measure dissolved oxygen at a first sampling frequency. The second probe may be identified as a reference probe that may measure dissolved oxygen at a second sampling frequency. In an embodiment, the frequency of sampling of the first probe may be greater than the sampling frequency of the second probe. It should be understood that while one probe is identified as a trend probe and one probe is identified as a reference probe, the probe themselves may include the same circuitry and may be interchangeable. In other words, the probes may be the same make and model and may include all the same circuitry and may be interchangeable, with the only exception being that one is identified as a trend probe and one is identified as a reference probe for purposes of the measurement device system.

In an embodiment, the probes may be fully or at least partially disposed in the volume of aqueous solution. For example, if the aqueous solution is introduced into a chamber having one or more probes, the aqueous solution may at least partially cover the one or more probes. As another example, the one or more probes may be partially disposed within the chamber with the other portion of the probes outside the chamber. Thus, when the aqueous solution is introduced into the chamber it only covers the portion of the probes that are within the aqueous sample volume. In an embodiment, a portion of the LDO probe to measure dissolved oxygen may be disposed in the aqueous sample and other circuitry or components of the probe may be out of the aqueous sample. For example, the luminescent area of the LDO probe may be immersed in the volume of aqueous sample, while circuitry, wiring, components, or the like, may be above the surface of the aqueous volume and/or outside a wall of a vessel containing the aqueous volume.

At 202, in an embodiment, the system may measure a first value of dissolved oxygen of the volume of aqueous solution using a trend sensor. In an embodiment, the trend sensor performs measurements at a trend frequency, for example, at a measuring frequency that is commonly associated with dissolved oxygen measurements. The trend probe may be a LDO probe or sensor. In an embodiment, the systems may include more than one trend sensor. The one or more trend sensors and/or trend probes may be disposed either in close proximity to one another or distributed in location throughout an aqueous volume. In an embodiment, a system may monitor dissolved oxygen in a plurality of volumes of aqueous samples or multiple locations within an aqueous sample. The use of the term "first" or "second" is not intended to designate either a temporal indication of when the measurement is taken or a location of one sensor with respect to another. Rather, the terms "first" and "second" are merely used to distinguish between two different sensors.

Figure 3:
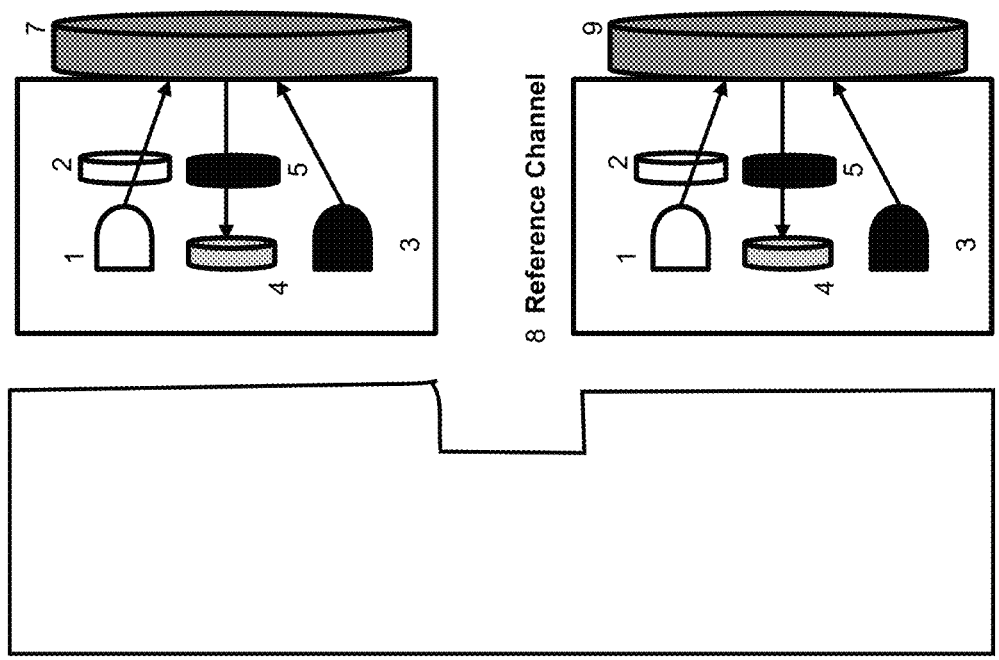
FIG. 3 illustrates a schematic diagram of an example dissolved oxygen measuring system.

Referring to FIG. 3, in an embodiment the measuring of dissolved oxygen using an LDO probe may use luminescent techniques. For example, the trend sensor 7 may have a sensitive luminescent coated area that is exposed to the aqueous sample to be measured. The measuring LED may emit a pulse of blue light from a blue LED 1 which passes through a blue filter 2 irradiating the back of an oxygen sensitive area of a trend sensor 7. The oxygen sensitive area may be coated with a coating material that reacts with luminescence and emits a pulse of red light. The red light may pass through a red filter 5 and to a detector 4. The probe may also contain a red LED 3.

The luminescent coating may be capable of measuring both an intensity and a timing of a pulse of light. If oxygen is present in a sample, which may be in contact with the coating, then the intensity and timing of the luminescent light emission may be changed. In other words, the more oxygen molecules that come into contact with the coating may change an intensity and time delay of the luminescent light emission. As more oxygen molecules are detected, the intensity may be lowered and the duration of the red radiation may become shorter. Changes to intensity and duration may be plotted in a profile curve and associated with a dissolved oxygen measurement. The trend probe and associated channel may provide a dissolved oxygen measurement as the oxygen level increases, decreases, or does not change over shorter periods of time as compared to a reference sensor. In other words, the trend sensor/probe may be used for a continuous monitoring of a sample as compared to a frequency of monitoring of a reference sensor.

At 203, the system may measure a second value of dissolved oxygen in the volume of aqueous solution using a reference sensor. In an embodiment, the reference sensor takes measurements at a reference frequency, which is generally a lower frequency than the trend frequency. In other words, the reference probe does not take measurements as frequently as the trend probe. The fact that the reference probe does not take measurements as frequently allows the components, for example, the coating of the reference probe, to be exposed to light less often due to a lower measurement frequency. Therefore, the components degrade less quickly due to the lower measurement frequency. The reference probe may be a LDO probe or sensor. In an embodiment, the system may have more than one reference sensor and/or reference probe. As with the trend sensors, the one or more reference sensors may be disposed either in close proximity to one another or distributed in location throughout an aqueous volume. However, the reference sensors and/or probes may be in close proximity to a corresponding trend sensor and/or probe.

Referring to FIG. 3, in an embodiment the measuring of dissolved oxygen using an LDO probe may use luminescent techniques. For example the reference sensor 9 may have a sensitive luminescent coated area that is exposed to the aqueous sample to be measured. The measuring LED may emit a pulse of blue light from a blue LED 1 which passes through a blue filter 2 irradiating the back of an oxygen sensitive area of a reference sensor 9. The oxygen sensitive area may be coated with a coating material that reacts with luminescence and emits a pulse of red light. The red light may pass through a red filter 5 and to a detector 4. The probe may also contain a red LED 3.

The luminescent coating may be capable of measuring both an intensity and a timing of a pulse of light. If oxygen is present in a sample, which may be in contact with the coating, then the intensity and timing of the luminescent light emission may be changed. In other words, the more oxygen molecules that come into contact with the coating may change an intensity and time delay of the luminescent light emission. As more oxygen molecules are detected, the intensity may be lowered and the duration of the red radiation may become shorter. Changes to intensity and duration may be plotted in a profile curve and associated with a dissolved oxygen measurement. The reference probe and associated channel may provide a dissolved oxygen measurement as the level increases, decreases, or does not change over longer periods of time as compared to a trend sensor. In other words, the reference sensor may be used for an intermittent monitoring of a sample as compared to a trend sensor.

In an embodiment, a reference sensor may be exposed to light in an intermittent manner. LDO probes may require exposure to light illumination for the luminescent area of the sensor to determine a level of dissolved oxygen in a volume of aqueous sample. LDO probes may undergo photo-bleaching when exposed to light. This photo-bleaching may degrade the luminescent material on the luminescent area of the sensor. Photo-bleaching may also decalibrate a probe/sensor and yield incorrect measurements of dissolved oxygen in a sample. Therefore, prevention of exposure to light of a reference sensor may preserve the luminescent material and "save" the sensor from photo-bleaching as quickly. A reference sensor may be used intermittently or at a frequency lower than a trend electrode to recalibrate a trend sensor.

The reference electrode may be shielded from light and subsequent photo-bleaching using multiple methods. A reference electrode may have all emitting LEDs or light sources that fall upon the luminescent material of the reference sensor turned off or unused. A reference sensor may have a moveable light shield to protect the luminescent area of the reference sensor from exposure to a light source. In an embodiment, a trend sensor and a reference sensor may have distinct light paths such that shunting light from contacting a reference sensor involves removing the light source in the reference probe light path. Other methods for shielding the luminescent material of the reference probe are contemplated and possible. Alternatively, the trend sensor and the reference sensor may be contained on a single substrate and represented by two or more luminescent materials that are each excited by different wavelengths. In this way, when a first wavelength is used that excites the trend sensor, the reference sensor is not excited by the same wavelength, thereby decreasing the rate of degradation of the reference sensor. When a reference measurement is needed, the system would provide a wavelength necessary for exciting the reference sensor luminescent material.

In an embodiment, the reference sensor may be programmed to measure after a certain number of measurements of a trend sensor. In an embodiment, the reference sensor may be programmed to measure after a certain amount of time. The reference frequency may be adjusted by a user or by system control. The reference frequency may be adjusted based upon a difference between a measurement by a trend sensor and a reference sensor. For example, if a level of dissolved oxygen as measured by a reference sensor and a trend sensor reaches a threshold, then the reference sensor may obtain measurements at a higher frequency to calibrate a trend sensor. For example, a trend sensor may measure dissolved oxygen at a higher frequency as compared to a reference sensor. Thus, a trend sensor may be exposed to and photo-bleached by light. In an embodiment, a measurement from a reference sensor which may have undergone less photo-bleaching may be used to calibrate a more highly photo-bleached trend sensor.

At 204, the system may determine whether the first value should be corrected based upon the second value. This determination may be made by determining if the difference between the first value, corresponding to the measurement generated by the trend probe, and the second value, corresponding to the measurement generated by the reference probe, is above a predetermined threshold. For example, the system may determine that the first value should be corrected if the difference between the first value and the second value is greater than a tolerance value. The determination may also be made based upon a predetermined time frame expiring. For example, the system may be programmed to correct the first value every day, week, or the like. The determination may also be made based upon a predetermined number of measurements being made. For example, the system may determine that the first value should be corrected after the trend probe has made a particular number of measurements. As another example, the system may receive information indicating a number of measurement cycles that result in the trend probe becoming uncalibrated. Accordingly, the system may correct the first value when that number of measurement cycles has passed. Other methods of determining whether the first value should be corrected are possible and contemplated.

If the system determines that the first value should be corrected using or based upon the second value, the system may correct the first value using or based upon the second value at 205. In other words, the second value of dissolved oxygen as measured by a reference sensor may be used to correct a first value of dissolved oxygen as measured by a trend sensor, thereby calibrating or correcting the trend sensor. In an embodiment, a trend sensor may be recalibrated to the value of dissolved oxygen of a reference sensor. In an embodiment, the trend sensor may be calibrated by using data collected under known conditions which plot the degradation of an LDO sensor. For example, in a test environment a sensor may be exposed to similar aqueous environments such as light exposure, aqueous sample components, temperature, salinity, turbidity, alkalinity, pressure, or the like. Test data may then be used to plot a curve of loss of calibration over time. Methods for calibration that use reference sensor data and that do not use reference sensor data may be used in any combination to calibrate a trend sensor. In an embodiment, there may be a plurality of trend sensors and a plurality of reference sensors. Additionally or alternatively, measurements from one or more of reference sensors may be used to calibrate one or more trend sensors.

If, at 204, the system determines that the first value does not need to be corrected based upon the second value, the system may not perform a correction or calibration at 206. In an embodiment, the lower frequency reference sensor measurement may comport with the higher frequency trend sensor measurement of dissolved oxygen. In this case, since no correction or calibration is required, the system will continue to measure dissolved oxygen through measurement of the one or more trend sensors.

In an embodiment, the system may connect to a communication network. The system may alert the user or the network. This alert may occur whether a correction of a trend sensor is required or not. An alert may be in a form of audio, visual, data, storing the data to a memory device, sending the output through a connected or wireless system, printing the output or the like. If a correction of a trend sensor is required the system may log information such as the sensor location, the nature of the corrective action, geographical location, time, date, number of sensor cycles, or the like. The alert or log may be automated, meaning the system may automatically output whether a correction was required or not. The system may also have associated alarms, limits, or predetermined thresholds. For example, if a frequency of recalibration of a sensor reaches a threshold, for example a sensor is requiring frequent recalibration, the system may trigger an alarm. Alarms or logs may be analyzed in real-time, stored for later use, or any combination thereof.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device such as illustrated in FIG. 1, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring dissolved oxygen of an aqueous sample, comprising:
   introducing an aqueous sample into a measurement device comprising at least two dissolved oxygen sensors, wherein at least one of the at least two dissolved oxygen sensors comprises a trend sensor and at least another of the at least two dissolved oxygen sensors comprises a reference sensor, wherein the trend sensor and the reference sensor each comprise a distinct luminescent coating material area and a source of illumination emitting UV excitation light;

measuring trend dissolved oxygen levels of the aqueous sample using the trend sensor, wherein the trend sensor performs dissolved oxygen level measurements at a trend frequency;

measuring reference dissolved oxygen levels using the reference sensor, wherein the reference sensor performs dissolved oxygen level measurements at a reference frequency, the reference frequency being less than the trend frequency reducing photobleaching of the reference sensor;

increasing the reference frequency in response to a difference between measurements by the trend sensor and the reference sensor, and correcting the trend dissolved oxygen levels based upon the reference dissolved oxygen levels.

2. The method of claim 1, wherein the measurement sensor and the trend sensor are contained in a single measurement device.

3. The method of claim 1, wherein the trend sensor and the reference sensor receive emitted UV light from different light paths.

4. The method of claim 1, wherein the reference sensor is shielded from emitted UV light for a periodic length of time.

5. The method of claim 1, further comprising calibrating the trend sensor and the reference sensor.

6. The method of claim 1, wherein the measuring reference dissolved oxygen levels occurs after a predetermined number of measuring trend dissolved oxygen levels occurs.

7. The method of claim 1, wherein the correcting further comprises comparing the trend dissolved oxygen levels to a database of trend dissolved oxygen levels data and wherein the correcting the trend dissolved oxygen levels is based upon the database of trend dissolved oxygen levels data.

8. The method of claim 1, further comprising notifying a user of a characteristic of the trend sensor, wherein the characteristic is identified based upon the reference dissolved oxygen levels.

9. A measurement device for measuring dissolved oxygen of an aqueous sample, comprising:
at least one chamber;
at least two dissolved oxygen sensors each having a luminescent coating;
at least one source of illumination emitting UV excitation light;
a processor; and
a storage device having code stored therewith, the code being executable by the processor and providing instructions to:
introduce, using a pump, an aqueous sample into the measurement device comprising at least two dissolved oxygen sensors, wherein at least one of the at least two dissolved oxygen sensors comprises a trend sensor and at least another of the at least two dissolved oxygen sensors comprises a reference sensor, wherein the trend sensor and the reference sensor each comprise a distinct luminescent coating material area and a source of illumination emitting UV excitation light;
measure trend dissolved oxygen levels of the aqueous sample using the trend sensor, wherein the trend sensor performs dissolved oxygen level measurements at a trend frequency;
measure reference dissolved oxygen levels using the reference sensor, wherein the reference sensor performs dissolved oxygen level measurements at a reference frequency, the reference frequency being less than the trend frequency reducing photobleaching of the reference sensor;
increase the reference frequency in response to a difference between measurements by the trend sensor and the reference sensor; and
correct the trend dissolved oxygen levels based upon the reference dissolved oxygen levels.

10. The device of claim 9, wherein the measurement sensor and the trend sensor are contained in a single measurement device.

11. The device of claim 9, wherein the trend sensor and the reference sensor receive emitted UV light from different light paths.

12. The device of claim 9, wherein the instructions further comprise an instruction for the processor to turn off emitted UV light to the reference sensor for a periodic length of time.

13. The device of claim 9, further comprising an instruction for the processor to calibrate the trend sensor and the reference sensor.

14. The device of claim 9, wherein the measuring reference dissolved oxygen levels occurs after a predetermined number of measuring trend dissolved oxygen levels occurs.

15. The device of claim 9, wherein the correcting further comprises comparing the trend dissolved oxygen levels to a database of trend dissolved oxygen levels data and wherein the correcting the trend dissolved oxygen levels is based upon the database of trend dissolved oxygen levels data.

16. A product for measuring dissolved oxygen of an aqueous sample, comprising
a storage device having code stored therewith, the code being executable by a processor and providing instructions to:
introduce, using a pump, an aqueous sample into a measurement device comprising at least two dissolved oxygen sensors, wherein at least one of the at least two dissolved oxygen sensors comprises a trend sensor with a luminescent coating and at least another of the at least two dissolved oxygen sensors comprises a reference sensor with a luminescent coating, wherein the trend sensor and the reference sensor each comprise a distinct luminescent coating material area and a source of illumination emitting UV excitation light;
measure, using the trend sensor, a trend dissolved oxygen levels of the aqueous sample, wherein the trend sensor performs dissolved oxygen level measurements at a trend frequency based upon measurements of the trend sensor luminescent coating;
measure a reference dissolved oxygen levels using the reference sensor, wherein the reference sensor performs dissolved oxygen level measurements at a reference frequency, the reference frequency being less than the trend frequency reducing photobleaching of the reference sensor;
increase the reference frequency in response to a difference between measurements by the trend sensor and the reference sensor; and
correct, using the processor, the trend dissolved oxygen levels based upon the reference dissolved oxygen levels.

* * * * *